(12) United States Patent
Zinnanti

(10) Patent No.: US 9,456,866 B2
(45) Date of Patent: Oct. 4, 2016

(54) ELECTROSURGERY PROBES WITH SMOKE AND LIQUID EVACUATION

(71) Applicant: William J. Zinnanti, Santa Cruz, CA (US)

(72) Inventor: William J. Zinnanti, Santa Cruz, CA (US)

( * ) Notice: Subject to any disclaimer, the term of this patent is extended or adjusted under 35 U.S.C. 154(b) by 0 days.

(21) Appl. No.: 14/489,292

(22) Filed: Sep. 17, 2014

(65) Prior Publication Data

US 2015/0005761 A1  Jan. 1, 2015

Related U.S. Application Data

(63) Continuation-in-part of application No. 13/706,242, filed on Dec. 5, 2012, now Pat. No. 9,101,363.

(60) Provisional application No. 61/681,626, filed on Aug. 10, 2012.

(51) Int. Cl.
*A61B 18/14* (2006.01)
*A61B 18/00* (2006.01)

(52) U.S. Cl.
CPC ........ *A61B 18/1482* (2013.01); *A61B 18/1402* (2013.01); *A61B 2018/00107* (2013.01); *A61B 2018/00589* (2013.01); *A61B 2018/00601* (2013.01); *A61B 2018/141* (2013.01); *A61B 2018/144* (2013.01); *A61B 2018/1407* (2013.01); *A61B 2018/1412* (2013.01); *A61B 2018/1417* (2013.01); *A61B 2018/1495* (2013.01); *A61B 2218/002* (2013.01); *A61B 2218/007* (2013.01); *A61B 2218/008* (2013.01)

(58) Field of Classification Search
USPC ................... 606/41, 45, 32, 27–28
See application file for complete search history.

(56) References Cited

U.S. PATENT DOCUMENTS

| 5,300,069 | A | * | 4/1994 | Hunsberger | A61B 18/1482 606/29 |
|---|---|---|---|---|---|
| 7,276,062 | B2 | * | 10/2007 | McDaniel | A61M 25/0138 606/41 |
| 7,329,253 | B2 | | 2/2008 | Brounstein et al. | |
| 7,569,053 | B2 | * | 8/2009 | Eggers | A61B 18/1402 606/41 |
| 2004/0024397 | A1 | | 2/2004 | Griffin, III et al. | |
| 2007/0106292 | A1 | * | 5/2007 | Kaplan | A61B 18/1492 606/41 |
| 2010/0205802 | A1 | | 8/2010 | Huseman | |
| 2011/0264086 | A1 | * | 10/2011 | Ingle | A61B 18/1492 606/33 |
| 2013/0012934 | A1 | | 1/2013 | Manwaring et al. | |

* cited by examiner

*Primary Examiner* — Paula J Stice
(74) *Attorney, Agent, or Firm* — Cardinal Law Group

(57) ABSTRACT

An electrosurgery probe comprises tip, mid-, and electrical contact segments. The mid-segment is a tube open at one end, closed at the other, and an interior flow passage. An opening formed through the wall of the tube adjacent to the closed end of the mid-segment and fluidly communicating with the interior flow passage. An electrosurgery system includes the electrosurgery probe and an electrosurgery handpiece. The handpiece comprises an elongate body segment and an exhaust cap attached to the body segment. A main flow passage extends longitudinally through the handpiece, and a second passage extends longitudinally through a distal portion of the body segment. In use, the probe is removably disposed in the handpiece such that the electrical contact segment is positioned within the second passage and the mid-segment opening is positioned within the exhaust cap and in fluid communication with the main flow passage.

9 Claims, 6 Drawing Sheets

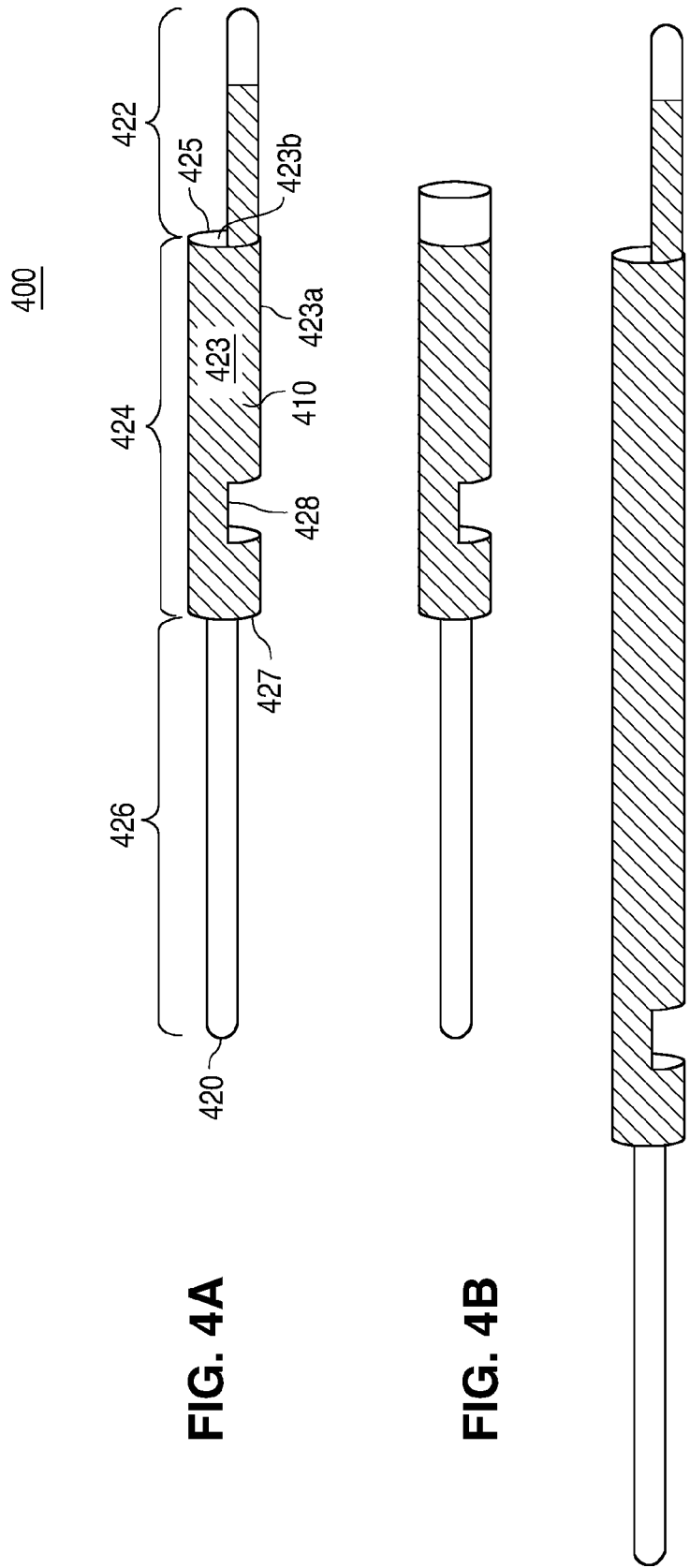

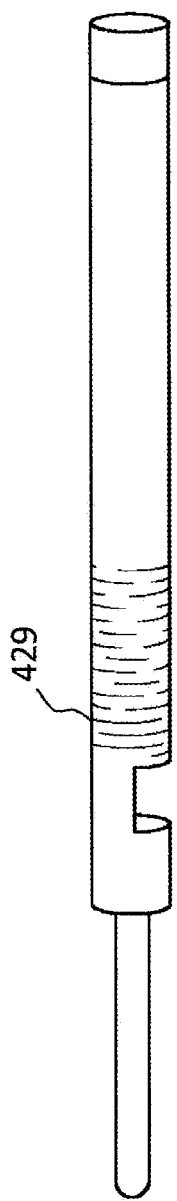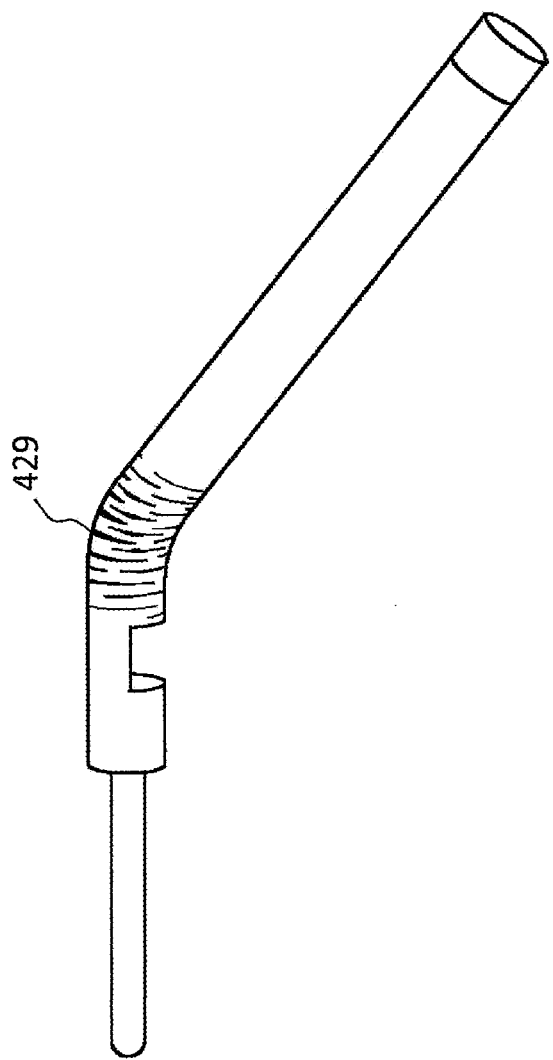
FIG. 4D
FIG. 4E

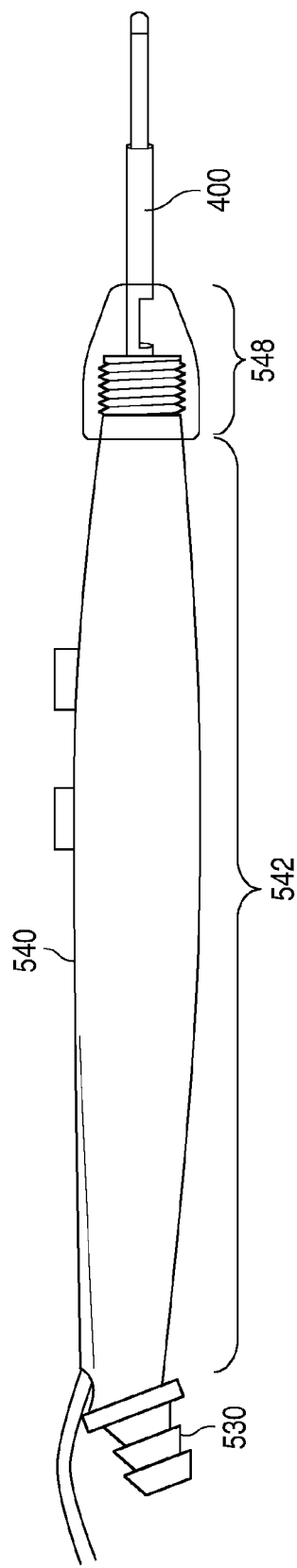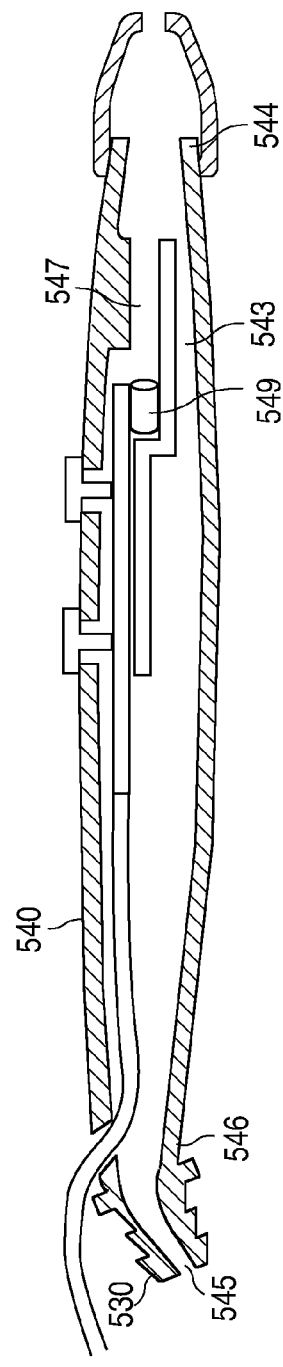
FIG. 5A
FIG. 5B

ELECTROSURGERY PROBES WITH SMOKE AND LIQUID EVACUATION

CROSS REFERENCE TO RELATED APPLICATIONS

This application is a continuation-in-part of U.S. patent application Ser. No. 13/706,242, filed Dec. 5, 2012, now U.S. Pat. No. 9,101,363 B2 issued Aug. 11, 2015, and claims the benefit of U.S. Provisional Application No. 61/681,626, filed Aug. 10, 2012, both of which are incorporated herein by reference in their entirety for all purposes.

TECHNICAL FIELD

This invention relates generally to surgical instruments. More particularly, the invention relates to electrosurgery probes and electrosurgery probe systems that provide removal of smoke, liquids, and debris during surgical operations.

BACKGROUND OF THE INVENTION

In certain deep surgical procedures, it is necessary to operate through a small opening into the body. These surgeries commonly employ specula (medical instruments for dilating a bodily passage or cavity) with built-in tubes to remove smoke from the surgical site during procedures such as laser or electrosurgical excision or cauterization. Additionally, a separate suction tube and/or irrigation source may be introduced for the purpose of removing smoke and debris from, or irrigation of, the surgical site. Tubing used to remove smoke and debris or to provide irrigation can obstruct the surgical site and impede visualization. Therefore, it is preferable to avoid having these additional tubes at the surgical site.

Systems used in electrosurgery procedures (also referred to herein as electrosurgical procedures) typically comprise a handpiece and interchangeable electrodes or probes. Electrosurgery probes consist of a tip that contacts tissue at the surgical site, a shaft of a given length, and a connector end that is inserted into the handpiece. The tips are made in many different shapes and sizes, including blade, ball tip, needle tip, and thin wire loops.

Prior art electrosurgery systems that provide evacuation and/or irrigation have a variety of disadvantages. For example, electrosurgery devices with incorporated suction were previously described in U.S. Pat. No. 2,888,928 to Seiger, U.S. Pat. No. 3,828,780 to Morrison, and U.S. Pat. No. 4,562,838 to Walker. These devices comprise a hollow metal conductive tube covered by insulation. The hollow metal tube carries the suction and ends in a blunt tip. Smoke enters the metal tube through the blunt tip that is formed by one end of the tube and is evacuated through the other end of the metal tube, flowing through the tube from one end to the other. This design is limited to a single tip that can perform coagulation but not cutting and requires a disposable handpiece with a smoke evacuation channel running through the handpiece.

U.S. Pat. No. 5,234,428 to Kaufman, U.S. Pat. No. 5,242,442 to Hirschfeld, and U.S. Pat. No. 8,057,470 to Lee et al. describe devices that include a smoke suction tube that surrounds or is applied next to a standard detachable electrode or blade. These devices also require a disposable handpiece with a smoke evacuation channel running through the handpiece.

Other patents for electrosurgery systems with incorporated smoke evacuation include U.S. Pat. No. 5,836,944 to Cosmescu, U.S. Pat. No. 5,224,944 to Elliott, and U.S. Pat. No. 6,146,353 to Platt. These patents describe a moveable or detachable shroud or tube that covers or lies next to the electrosurgery probe and provides the smoke evacuation conduit. Exchanging of electrodes or probes to provide different tips requires removal and/or adjustment and readjustment of the smoke evacuation conduit.

Therefore, it would be desirable to provide an electrosurgery probe and electrosurgery system that overcome the aforementioned and other disadvantages.

SUMMARY OF THE INVENTION

One aspect of the present invention is an electrosurgery probe. The probe comprises a conductive element that itself comprises a tip segment, a mid-segment, and an electrical contact segment. The mid-segment has an open distal end and a closed proximal end and comprises a tube having a wall and an interior flow passage. The mid-segment has an opening formed through the wall of the tube adjacent to the proximal end of the mid-segment, the opening in fluid communication with the interior flow passage.

Another aspect of the present invention is an electrosurgery system comprising an electrosurgery handpiece and a first electrosurgery probe. The electrosurgery handpiece comprises an elongate body segment and an exhaust segment. A main flow passage extends longitudinally through the handpiece. A second passage extends longitudinally through a distal portion of the body segment, the second passage terminating in an electrical contact. The exhaust segment has a cross-sectional diameter greater than a cross-sectional diameter of the main flow passage.

The first electrosurgery probe comprises a conductive element, the conductive element comprising a tip segment, a mid-segment, and an electrical contact segment. The mid-segment comprises a tube having a wall and an interior flow passage. The mid-segment has an open distal end, a closed proximal end, and an opening formed through the wall of the tube adjacent to the proximal end of the mid-segment, the opening in fluid communication with the interior flow passage. The electrical contact segment and a portion of the mid-segment are removably disposed within the electrosurgery handpiece such that the electrical contact segment is positioned within the second passage and the mid-segment opening is positioned within the exhaust segment.

Yet another aspect of the present invention is a method of performing an electrosurgery procedure. In the method, an electrosurgery system is provided that includes an electrosurgery handpiece, a dissecting electrosurgery probe, and a suction/coagulator electrosurgery probe. The dissecting electrosurgery probe is attached to the handpiece. Dissection is performed at an electrosurgery site using the dissecting electrosurgery probe. The dissecting electrosurgery probe is detached from the handpiece, and the suction/coagulator electrosurgery probe is attached to the handpiece. One or both of suction and coagulation is performed at the electrosurgery site.

The aforementioned and other features and advantages of the invention will become further apparent from the following detailed description of the presently preferred embodiments, read in conjunction with the accompanying drawings, which are not to scale. The detailed description and drawings are merely illustrative of the invention, rather than limiting, the scope of the invention being defined by the appended claims and equivalents thereof.

BRIEF DESCRIPTION OF THE DRAWINGS

FIG. 4A is a perspective view of an electrosurgery probe or electrosurgery probe conductive element in accordance with the present invention, the electrosurgery probe or electrosurgery probe conductive element having a blade tip;

FIG. 4B is a perspective view of an electrosurgery probe or electrosurgery probe conductive element in accordance with the present invention, the electrosurgery probe or electrosurgery probe conductive element having a blunt tip;

FIG. 4C is a perspective view of an electrosurgery probe or electrosurgery probe conductive element in accordance with the present invention, the electrosurgery probe or electrosurgery probe conductive element having an elongated mid-segment and a blade tip;

FIGS. 4D and 4E are perspective views of an electrosurgery probe or electrosurgery probe conductive element in accordance with the present invention, the electrosurgery probe or electrosurgery probe conductive element having a flexible mid-segment;

FIG. 5A is a perspective view of another electrosurgery system in accordance with the present invention;

FIG. 5B is a cutaway view of the handpiece of the system of FIG. 5A;

DETAILED DESCRIPTION OF THE PRESENTLY PREFERRED EMBODIMENTS

Figure 1A:
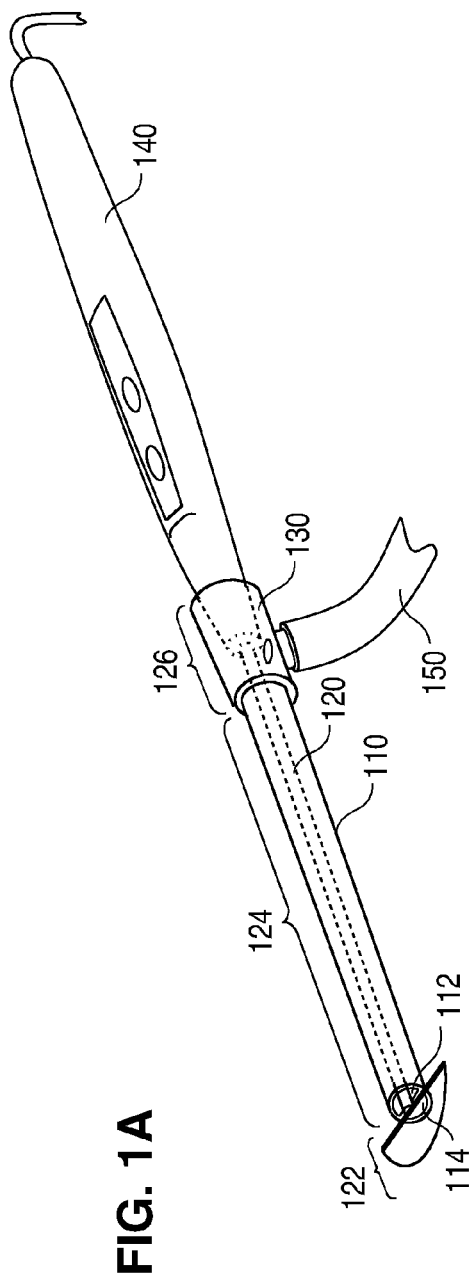
FIG. 1A is a perspective view of an electrosurgery system in accordance with the present invention.
Figure 1C:
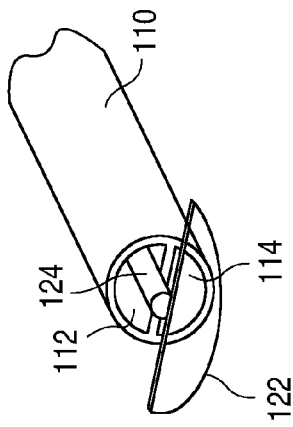
FIG. 1C is an enlarged view of a portion of the electrosurgery probe illustrated in FIGS. 1A and 1B.
Figure 1B:
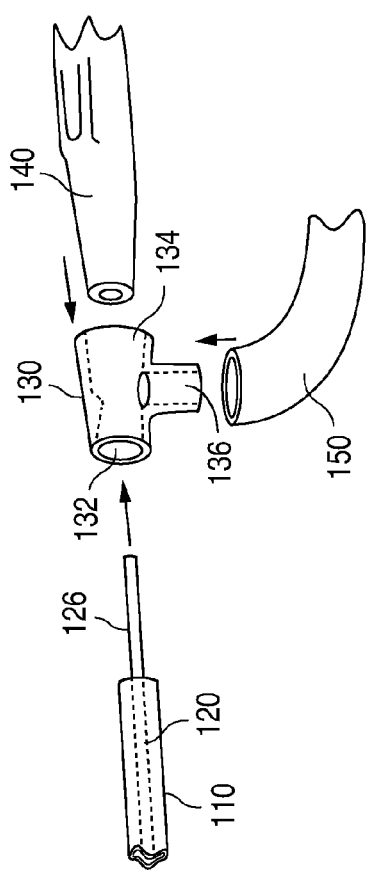
FIG. 1B is an exploded view of the system of FIG. 1A.

One aspect of the present invention is an electrosurgery probe. Electrosurgery probes in accordance with one embodiment of the present invention are illustrated in FIGS. 1A and 1B as elements of an electrosurgery system and in FIGS. 2A-2F independent of the system. Each electrosurgery probe of the present embodiment comprises an insulated shaft 110 and a conductive element 120.

As illustrated in FIGS. 1A, 1B, and 2A-2F, shaft 110 is an elongated, substantially cylindrical member. The length of shaft 110 is variable depending on the intended use of the electrosurgery probe; the shaft must extend out from a connector 130 just far enough to allow space for flow of suction or irrigation when the electrosurgery probe is properly seated in connector 130 and an electrosurgery handpiece 140, as described below. The shaft need not be cylindrical, with virtually any elongated shape being acceptable. Because the conductive element disposed within shaft 110 is electrically conductive, the shaft is made of an insulating (e.g., dielectric or nonconductive) material having sufficient rigidity to allow the tip segment of the electrosurgery probe to be applied to tissue appropriately during a surgical procedure. The insulating shaft shields from inadvertent lateral burning of tissue along the sides of the electrosurgery probe. This is especially important with elongated probes for deep procedures in body cavities. The insulating material is typically molded plastic or heat-shrink tubing. Suitable materials include elastomers and polymers such as polydimethylsiloxane (PDMS), polymethylmethacrylate (PMMA), polycarbonate, polytetrafluoroethylene (PTFE), polyvinylchloride (PVC), polysulfone, polystyrene, polymethylpentene, polypropylene, polyethylene, polyvinylidine fluoride, ABS (acrylonitrile-butadiene-styrene copolymer), cyclic-olefin polymer (COP), cyclic-olefin copolymer (COC), and other insulating materials that prevent or minimize conduction of both heat and electricity. The shaft may be, for example, an extruded or molded plastic tubing having multiple channels formed during the extrusion or molding process.

Figure 3A:
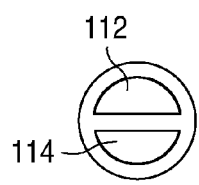
FIGS. 3A-3C provide cross-sectional views of a shaft of an electrosurgery probe in accordance with the present invention.
Figure 3B:
Figure 3C:
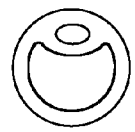

Shaft 110 includes at least a first channel 112 and a second channel 114. First channel 112 is substantially occupied by conductive element 120. Second channel 114 is open the entire length of the shaft and available for suction and/or irrigation supplied, for example, by a length of tubing 150 with which channel 114 is in fluid communication. Channels 112 and 114 are covered channels (i.e., lumens) that extend the entire length of shaft 110. FIGS. 3A-3C show various possible cross-sectional views of shaft 110, with channels 112 and 114 indicated in FIG. 3A. One skilled in the art will appreciate that FIGS. 3A-3C represent just a few of many possible cross-sectional configurations.

Conductive element 120 comprises a tip segment 122, a mid-segment 124, and an electrical contact segment 126, all of which can be seen in FIG. 1A. Tip segment 122 may assume a variety of different shapes such as, for example, a thin wire loop (FIGS. 1A and 1C at 122 and FIG. 2A at 122a) or blade tip (FIGS. 2D and 2F at 122d) for cutting, a ball tip (FIG. 2B at 122b) for coagulation after cutting, or a needle tip (FIGS. 2C and 2E at 122c) for transfer of concentrated energy into a limited area. Other shapes are, of course, possible. As is evident from FIGS. 2A-2F, each electrosurgery probe according to the current invention has a single tip shape. The entire electrosurgery probe can be exchanged for another electrosurgery probe during a surgical procedure if a different tip shape is desired. Mid-segment 124 and electrical contact segment 126 are typically a stainless steel rod or wire but may, alternatively, be constructed using any conductive material capable of enabling the probe to perform an electrosurgery procedure. Tip segment 122 may be constructed of the same material as the mid-segment and electrical contact segment; loop tips are also commonly fabricated from tungsten wire.

As seen in FIG. 1A, conductive element 120 is disposed in channel 112 such that tip segment 122 extends from a distal end of shaft 110, mid-segment 124 is within shaft 110, and electrical contact segment 126 extends from a proximal end of shaft 110. (The term "distal" is used herein to designate an end or portion nearest to the patient during use of the electrosurgery probe, and the term "proximal" is used herein to designate an end or portion nearest to the operator during use of the electro surgery probe.) During fabrication of the electrosurgery probe, conductive element 120 may be positioned in shaft 110 by being inserted into a fully formed shaft. Alternatively, where shaft 110 is an extruded or molded plastic tubing having multiple channels formed during the extrusion or molding process, the tubing may be extruded or molded directly over conductive element 120. Extrusion or molding of the shaft over the conductive element is particularly convenient where the mid-segment of the electrosurgery probe is curved or angled as seen in FIGS. 2E and 2F, respectively.

Another aspect of the present invention is an electrosurgery system. In one embodiment, the system is formed when a connector 130 serves as a common hub to bring together an electrosurgery probe such as has been described above, an electrosurgery handpiece 140, and a length of tubing 150. In the system, both the electrosurgery probe and handpiece 140 are removably attached to connector 130. The system may include multiple interchangeable electrosurgery probes to offer a variety of different electrosurgery tips such as can be seen in FIGS. 2A-2F.

As illustrated in FIGS. 1A and 1B, connector 130 is a T-connector having first, second, and third connection points 132, 134, and 136, respectively. While connector 130 is shown to have three connection points, the connector may, alternatively, have more than three connection points and may assume shapes other than that of the T-connector shown in FIGS. 1A and 1B. For example, connector 130 could be a Y-connector. Connector 130 is preferably made of a soft rubber or plastic material but can be made of other materials that are conformable to one or both of the shaft 110 of the electrosurgery probe and the handpiece 140. Connector 130 is of sufficient size to adapt to different sizes and shapes of standard electrosurgery handpieces.

As indicated in FIGS. 1A and 1B, a proximal portion of the electrosurgery probe is removably disposed within connector 130 at connection point 132 such that electrical contact segment 126 of the electrosurgery probe is fully within connector 130 and a substantially air-tight connection is made between shaft 110 and connector 130. Connection point 132 is illustrated in FIGS. 1A and 1B as a female connection point; however, it will be appreciated that shaft 110 could be constructed such that a portion of shaft 110 fits over a male connection point 132 rather than within a female connection point 132.

A distal portion of electrosurgery handpiece 140 is removably disposed within connection point 134 such that a substantially air-tight connection is made between the electrosurgery handpiece and the connector and such that electrical contact segment 126 of the electrosurgery probe is inserted into electrosurgery handpiece 140, thereby providing an electrical connection between the electrosurgery probe and electrosurgery handpiece 140. The electrosurgery handpiece may be any commercially available handpiece and may be, for example, either hand activated or foot activated. Thus, it is preferable that connection point 134 be a female connection point that can be slipped over the distal end of the desired handpiece. As mentioned previously, connector 130 may be constructed of a soft rubber or plastic, making the connector readily adaptable to various shapes and sizes of handpieces.

One end of a length of tubing 150 is either removably or permanently attached to connector 130 at connection point 136, which may be either a male (as illustrated) or female connection point. The other end of tubing 150 is attached to, for example, a vacuum source or an irrigation fluid source. Connector 130, the electrosurgery probe, and/or tubing 150 may be adapted such that both a vacuum source and an irrigation fluid source may be simultaneously connected to the electrosurgery probe via connector 130. Thus, channel 114 of the electrosurgery probe may be in fluid communication with a vacuum and/or irrigation fluid source via tubing 150 and connector 130.

Another embodiment of a conductive element can be seen at 420 in FIGS. 4A-4E. Conductive element 420 comprises a tip segment 422, a mid-segment 424, and an electrical contact segment 426.

In the present embodiment, both tip segment 422 and mid-segment 424 are segments of a hollow tube 423 (i.e., a tube having a wall 423a and an interior flow passage 423b). Tip segment 422 is formed into hollow tube 423 by, for example, laser cutting the desired shape into the distal end of the tube. Desired shapes may be, for example, a blade tip as seen in FIGS. 4A and 4C or a blunt tip as seen in FIGS. 4B, 4D, and 4E. Other tip shapes are possible. In this embodiment, the wall of tube 423 is constructed using any conductive material capable of performing an electrosurgery procedure. One such conductive material is stainless steel.

Figure 2A:
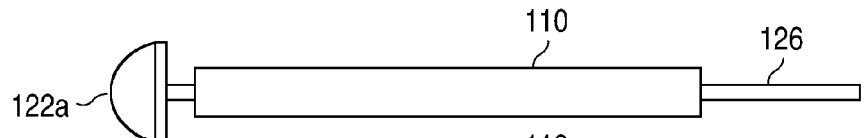
FIG. 2A is a perspective view of an electrosurgery probe in accordance with the present invention, the electrosurgery probe having a thin wire loop tip.
Figure 2B:
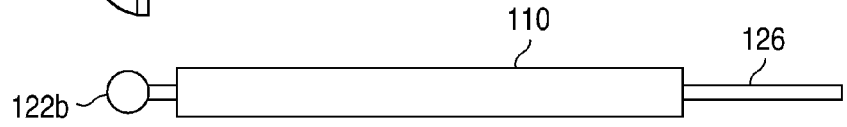
FIG. 2B is a perspective view of an electrosurgery probe in accordance with the present invention, the electrosurgery probe having a ball tip.
Figure 2C:
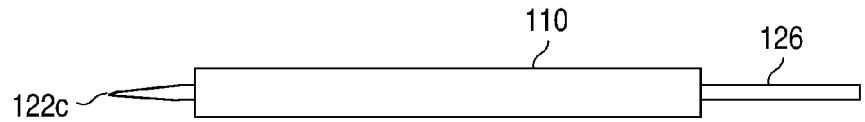
FIG. 2C is a perspective view of an electrosurgery probe in accordance with the present invention, the electrosurgery probe having a needle tip.
Figure 2D:
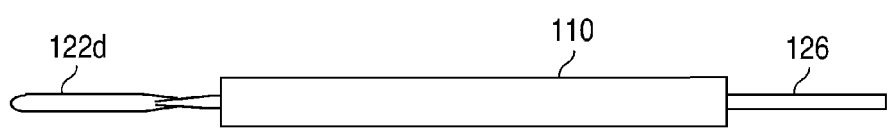
FIG. 2D is a perspective view of a electrosurgery probe in accordance with the present invention, the electrosurgery probe having a blade tip.
Figure 2E:
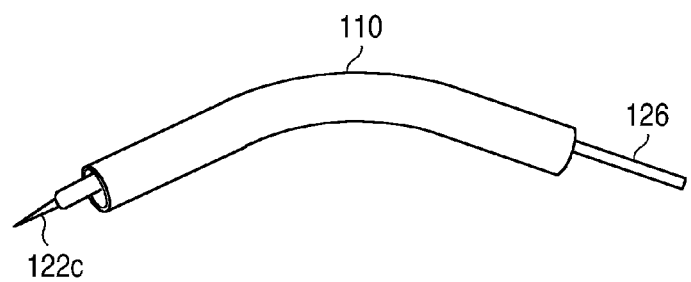
FIG. 2E is a perspective view of an electrosurgery probe in accordance with the present invention, the electrosurgery probe shown curved.
Figure 2F:
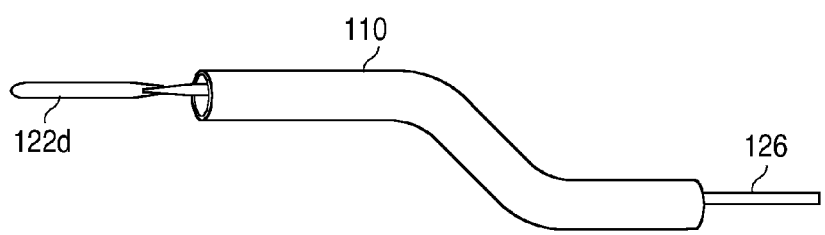
FIG. 2F is a perspective view of an electrosurgery probe in accordance with the present invention, the electrosurgery probe shown angled.

Alternatively, the mid-segment may comprise a hollow tube, while the tip segment may be a blade (or other shape, including ball and needle such as can be seen in FIGS. 2B and 2C) that is formed separately and attached to the mid-segment by, for example, welding or any other appropriate attachment process. Where the tip segment is formed separately, the wall of the hollow tube forming the mid-segment need not itself comprise a conductive material if a conductive path is provided between the tip segment and the electrical contact segment by a conductive element such as, for example, a thin strip of metal or a wire extending the length of the mid-segment and connecting to both the electrical contact segment and the tip segment.

The mid-segment may be any desired length as illustrated by FIGS. 4A through 4C, allowing for use in both superficial and deep procedures. The inner diameter of the hollow tube in the area of the mid-segment is preferably large enough to provide adequate suction for removing blood and other fluids and debris from the procedure site. The distal end 425 of mid-segment 424 is open, while the proximal end 427 is closed. At least one opening 428, e.g., a notch as seen in FIGS. 4A-4E, is cut or otherwise formed through wall 423a adjacent to (i.e., at or near) the proximal end of mid-segment 424. Opening 428 is in fluid communication with interior flow passage 423b and is preferably at least as large as the opening at the distal end of the conductive element (e.g., at least as large as the cross-sectional area of the interior flow passage) to avoid restriction of flow according to Bernoulli's principle. More than one opening 428 may be formed through the wall of the mid-segment. For example, it may be advantageous to provide a second opening 428 rotated 180° about the external surface of the tube from the location of the first opening 428.

The mid-segment may include a series of cuts 429 extending through the wall of the tube as illustrated in FIGS. 4D and 4E. The cuts result in a flexible mid-segment, allowing the tube to be bent into any desired shape without significantly reducing the cross-sectional area of the interior flow passage. Preferably the tube is conductive, e.g., comprises a metal. FIGS. 4D and 4E show cuts within a limited portion of the mid-segment; however, the cuts could extend over any desired portion of the mid-segment, permitting the mid-segment to be shaped not only as seen in FIG. 4E, but also into additional shapes such as, for example, those seen in FIGS. 2E and 2F. The series of cuts preferably forms an interrupted spiral pattern; i.e., the series of cuts goes around the tube approximately ⅓ of the circumference of the tube and ends and then begins again. The cuts preferably have a 0.02-inch to 0.04-inch pitch, the pitch being the nominal distance between two adjacent cuts.

Electrical contact segment 426 may be a separate piece welded or otherwise affixed to the hollow tube forming tip segment 422 and mid-segment 424. Alternatively, electrical contact segment 426 may be an extension of the hollow tube where the hollow tube is itself conductive. Electrical contact segment 426 comprises a conductive material capable of enabling the probe to perform an electrosurgery procedure. For example, where the probe is used for performing a cautery procedure, the conductive material is capable of heating tip segment 422 to an appropriate temperature for performing the procedure (e.g., between approximately 350° C. and 1200° C.).

The mid-segment may include an insulating (e.g., dielectric or nonconductive) coating 410 disposed over an external surface of the wall of the hollow tube forming the mid-segment. Suitable materials for insulating coating 410 include elastomers and polymers such as polydimethylsiloxane (PDMS), polymethylmethacrylate (PMMA), polycarbonate, polytetrafluoroethylene (PTFE), polyvinylchloride (PVC), polysulfone, polystyrene, polymethylpentene, polypropylene, polyethylene, polyvinylidine fluoride, ABS (acrylonitrile-butadiene-styrene copolymer), cyclic-olefin polymer (COP), cyclic-olefin copolymer (COC), and other insulating materials that prevent or minimize conduction of both heat and electricity. In one example, the insulating coating is disposed over at least a portion of an external surface of mid-segment 424 and may be, for example, a heat-shrink plastic. A polyolefin insulation may also be applied as well as high-temperature Teflon® (polytetrafluoroethylene [PTFE]) for extra heat resistance.

Insulating coating 410 plus conductive element 420 together may form an electrosurgery probe 400 as indicated in FIG. 4A. Note that an insulating coating may not be a required element of electrosurgery probe 400, for example when the wall of the hollow tube forming the mid-segment is itself non-conductive. Where an insulating coating is not necessary, the conductive element alone serves as an electrosurgery probe. Coated or uncoated conductive elements having blade or needle tips typically serve as dissecting electrosurgery probes. Coated or uncoated conductive elements having blunt tips typically serve as suction/coagulator electrosurgery probes.

Figure 5C:
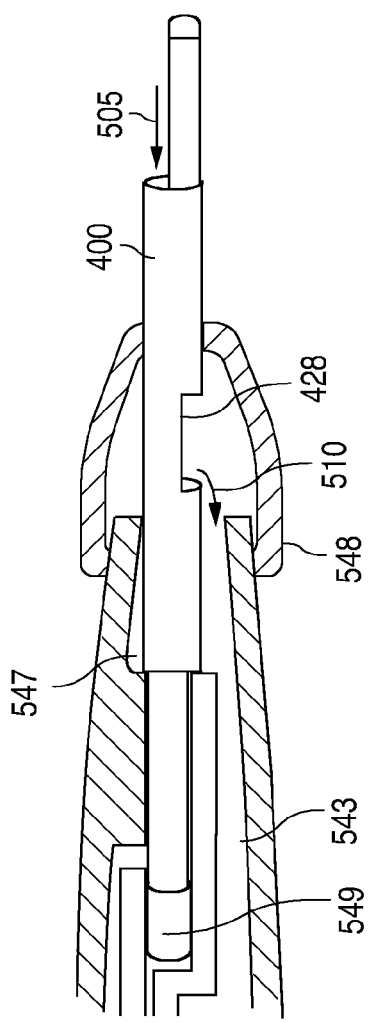
FIG. 5C is a cutaway view of a distal portion of the electrosurgery system of FIG. 5A enlarged to show direction of flow during evacuation of smoke and/or liquids or debris.
Figure 6:
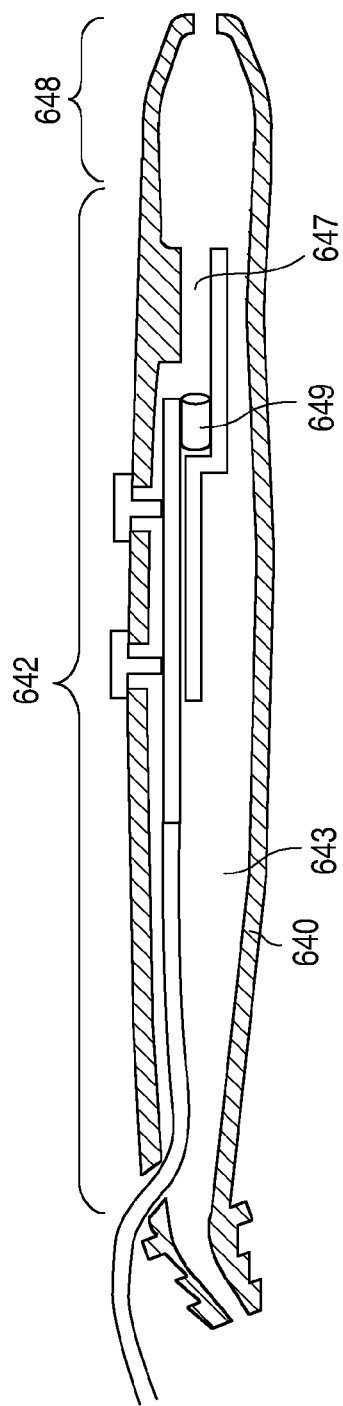
FIG. 6 is a side view of an alternative handpiece in accordance with the present invention.

The electrosurgery probes described above and illustrated in FIGS. 4A-4E may be combined with an electrosurgery handpiece such as is seen at 540 in FIGS. 5A-5C to form an electrosurgery system. Note that an alternative handpiece is illustrated in FIG. 6 and is described below. The electrosurgery system may include multiple interchangeable electrosurgery probes to offer a variety of different electrosurgery tips. A first electrosurgery probe may be removed and exchanged for a second electrosurgery probe during a surgical procedure.

Handpiece 540 comprises elongate body segment 542 and exhaust segment 548. Body segment 542 is typically constructed of a substantially rigid and nonconductive material such as ABS or PVC. A main flow passage 543 extends longitudinally through handpiece 540 from the distal end 544 of body segment 542 to an opening 545 adjacent to (i.e., at or near) the proximal end 546 of body segment 542. Opening 545 is in fluid communication with a vacuum source (i.e., a source of suction or negative pressure) via a connector 530.

A second passage 547 extends longitudinally through a distal portion of body segment 542 and terminates in an electrical contact 549. As illustrated, electrical contact 549 is a concentric electrical receptacle comprising a metal tube, for example a copper tube, that is split along at least a portion of its length, allowing the tube to expand sufficiently to receive the electrical contact segment of the desired electrosurgery probe. The copper tube is connected to a power source (not shown) when the electrosurgery system is in operation. Thus the copper tube provides a conductive path from the power source to electrical contact segment 426 via the copper tube and then on through mid-segment 424 to tip segment 422. Alternatively, electrical contact 549 may be any appropriate electrical contact known in the art, one such being simply an exposed end of an electric power cable.

When the electrosurgery system is in use, the electrical contact segment 426 of an electrosurgery probe 400 is removably disposed within handpiece 540 such that at least a portion of the electrical contact segment is within second passage 547 and in contact with electrical contact 549, thereby providing an electrical connection between electrosurgery handpiece 540 and electrosurgery probe 400. Second passage 547 may be tubular or may be a series of aligned rings or partial rings through which electrical contact segment 426 is directed to electrical contact 549. Both handpiece 540 and electrosurgery probe 400 are dimensioned to ensure correct positioning of electrical contact segment 426 within second passage 547.

As seen in FIGS. 5A-5C, exhaust segment 548 is a cap that is formed separately from body segment 542 and attached either permanently or removably to the distal end 544 of body segment 542 by any appropriate bonding or other attachment method. Exhaust cap 548 is constructed of a material such as PVC or silicone rubber that is capable of removably receiving an electrosurgery probe and forming a substantially air-tight seal between the electrosurgery handpiece and the electrosurgery probe.

Exhaust cap 548 is substantially hollow and has an interior cross-sectional diameter that is greater than a cross-sectional diameter of main flow passage 543. As is best seen in FIG. 5C, the handpiece and electrosurgery probe are dimensioned to ensure that opening 428 formed in mid-segment 424 is positioned within exhaust cap 548 when the electrosurgery probe is inserted into the handpiece. Positioning of opening 428 within exhaust cap 548 ensures that smoke and liquids can flow freely out of opening 428 and into main flow passage 543, providing fluid communication between the interior of exhaust cap 548 and main flow passage 543. Arrows 505 and 510 show the direction of flow through mid-segment 424 and into main flow passage 543. The material of cap 548 may be opaque, translucent, or transparent as seen in FIG. 5A. A transparent cap allows for easy visualization of clots or tissue that may clog the passage and require clearing. Transparency can also be useful for ensuring an electrosurgery probe is correctly inserted into the electrosurgery handpiece.

Alternative handpiece 640, illustrated in FIG. 6, comprises an elongate body segment 642 and an exhaust segment 648. As can be seen in FIG. 6, body segment 642 is similar to body segment 542, which has been described in detail above. However, in the embodiment illustrated in FIG. 6, exhaust segment 648 is an extension of body segment 642 and is formed simultaneously with and of the same material or materials as body segment 642. For example, both body segment 642 and exhaust segment 648 may be constructed of a material such as PVC that is capable of removably receiving an electrosurgery probe and forming a substantially air-tight seal between the electrosurgery handpiece and the electrosurgery probe.

As can be seen in FIG. 6, exhaust segment 648 is substantially hollow and has an interior cross-sectional diameter that is greater than a cross-sectional diameter of the main flow passage 643. Both handpiece 640 and the electrosurgery probe are dimensioned to ensure that opening 428 formed in mid-segment 424 of the electrosurgery probe is positioned within exhaust segment 648 when the electrosurgery probe is inserted into handpiece 640. Positioning of opening 428 within exhaust segment 648 ensures that smoke and liquids can flow freely out of opening 428 and into main flow passage 643, providing fluid communication between the interior of exhaust segment 648 and main flow passage 643.

In the present embodiment, when the electrosurgery system is in use, the electrical contact segment 426 of an electrosurgery probe 400 is removably disposed within handpiece 640 such that at least a portion of the electrical contact segment is within a second passage 647 and in contact with an electrical contact 649, thereby providing an electrical connection between electrosurgery handpiece 640 and electrosurgery probe 400. Second passage 647 may be tubular or may be a series of aligned rings or partial rings through which electrical contact segment 426 is directed to electrical contact 649 Both handpiece 640 and electrosurgery probe 400 are dimensioned to ensure correct positioning of electrical contact segment 426 within second passage 647.

In another embodiment, an electrosurgery system may be formed by combining a conductive element such as has been described above and illustrated at 420 in FIGS. 4A-4E with an electrosurgery handpiece such as is seen in FIGS. 1A and 1B. In the present embodiment, conductive element 420 is inserted into connection point 132 of connector 130. I.e., both shaft 110 and conductive element 120 in FIGS. 1A and 1B are replaced by a conductive element 420 where the mid-segment 424 is non-conductive, or by a combination of a non-conductive coating 410 and a conductive element 420 where the mid-segment 424 is conductive. Conductive element 420 is positioned within connector 130 such that tip segment 422 and a distal portion of mid-segment 424 extend from connector 130, and electrical contact segment 426 extends through connector 134 into electrosurgery handpiece 140. Opening 428 is positioned within connector 130 in fluid communication with connection point 136 and tubing 150. Preferably mid-segment 424 forms a substantially air-tight connection with connector 130 at connection point 132. In this embodiment, simultaneous smoke and liquid evacuation is possible.

Yet another aspect of the present invention is a method of performing an electrosurgery procedure. The method includes attaching to a connector, in any order, a first electrosurgery probe, an electrosurgery handpiece having an activator, and a first length of tubing that is in fluid communication with one or both of a vacuum source and an irrigation fluid source. The electrosurgery handpiece is connected to an electrical source either before or after the handpiece is attached to the connector. The resulting electrosurgery system is then activated by operating the activator of the handpiece (for example, either a hand or foot activator), and the system is used to perform an electrosurgery procedure. The method may further comprise removing the first electrosurgery probe from the connector and attaching a second electrosurgery probe to the connector. This step may be performed without removing the electrosurgery handpiece from the connector and also without removing the attached tube(s) from the connector. The method may also further comprise attaching a second length of tubing to the connector if both vacuum and irrigation are desired, the second length of tubing in fluid communication with one or both of a vacuum source and an irrigation fluid source.

In another method of performing an electrosurgery procedure, an electrosurgery system is provided that includes an electrosurgery handpiece, a dissecting electrosurgery probe, and a suction/coagulator electrosurgery probe. The dissecting electrosurgery probe is attached to the handpiece. Dissection is performed at an electrosurgery site using the dissecting electrosurgery probe. The dissecting electrosurgery probe is detached from the handpiece, and the suction/coagulator electrosurgery probe is attached to the handpiece. One or both of suction and coagulation is performed at the electrosurgery site.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. An electrosurgery probe, comprising:
an electrically-conductive element comprising a surgical tool tip segment, a mid-segment, and an electrical contact segment, the mid-segment comprising a hollow, unobstructed tube having a wall and an interior flow passage, the mid-segment having an open distal end and a closed proximal end, wherein the mid-segment is coupled at its distal end directly to the surgical tool tip segment and coupled at its closed proximal end directly to the electrical contact segment, the mid-segment further having an opening formed through the wall of the tube adjacent to the proximal end of the mid-segment, the opening in fluid communication with the interior flow passage, and wherein the surgical tool tip segment, the mid-segment and the electrical contact segment are all comprised of at least one electrically-conductive material to enable passage of electrical current from the surgical tool tip segment through the mid-segment to the electrical contact segment.

2. The electrosurgery probe of claim 1 further comprising a coating disposed over at least a portion of an external surface of the conductive element.

3. The electrosurgery probe of claim 2 wherein the coating comprises an insulating material selected from the group consisting of polydimethylsiloxane (PDMS), polymethylmethacrylate (PMMA), polycarbonate, polytetrafluoroethylene (PTFE), polyvinylchloride (PVC), polysulfone, polystyrene, polymethylpentene, polypropylene, polyethylene, polyvinylidine fluoride, ABS (acrylonitrile-butadiene-styrene copolymer), cyclic-olefin polymer (COP), cyclic-olefin copolymer (COC), and combinations thereof.

4. The electrosurgery probe of claim 1 wherein the opening in the mid-segment is at least as large as a cross-sectional area of the interior flow passage.

5. The electrosurgery probe of claim 1 wherein the tip segment includes one of a blade tip and a blunt tip.

6. The electrosurgery probe of claim 1 wherein the tip segment is formed into the hollow tube.

7. The electrosurgery probe of claim 1 wherein the tip segment is formed separately from the mid-segment and is attached to the mid-segment.

8. The electrosurgery probe of claim 1 wherein the tube includes a series of cuts extending through the wall of the tube, the cuts resulting in a flexible tube.

9. The electrosurgery probe of claim 8 wherein the series of cuts forms an interrupted spiral pattern.

\* \* \* \* \*